United States Patent [19]
Hulten

[11] 3,988,830
[45] Nov. 2, 1976

[54] PROXIMAL SOLDERING TABS FOR A DENTAL PROSTHETIC STRUCTURE

[76] Inventor: Olle Hulten, Rorsmansgatan 50, 216 11 Malmo, Sweden

[22] Filed: Apr. 23, 1975

[21] Appl. No.: 570,818

[52] U.S. Cl. .................................................. 32/12
[51] Int. Cl.² ........................................... A61C 5/08
[58] Field of Search ............................. 32/5, 12, 13

[56] References Cited
UNITED STATES PATENTS
2,672,686   3/1954   Herzberg ................................. 32/5

*Primary Examiner*—Robert Peshock
*Attorney, Agent, or Firm*—Friedman, Goodman & Teitelbaum

[57] ABSTRACT

Soldering tabs for investment molded crowns fabricated from non-precious metals and disposed on adjacent teeth, where each of the tabs is fabricated from a precious metal capable of being soldered. Each of the tabs includes tapering walls to define wedge-shaped portions for anchoring the respective tab in its associated crown. Adjacent tabs are disposed in their associated crowns at an outer wall thereof facing one another to permit the facing tabs to be soldered together to fix the adjacent crowns relative to each other. Each of the tabs is provided with threaded openings extending through each tab for receiving a threaded member to position the tab during investment molding of the crown and for receiving solder when the facing tabs are secured together.

9 Claims, 8 Drawing Figures

PROXIMAL SOLDERING TABS FOR A DENTAL PROSTHETIC STRUCTURE

BACKGROUND OF THE INVENTION

The present invention relates to tabs fabricated from metal capable of being soldered, and more particularly to soldering tabs fabricated from a precious metal for securing together investment molded crowns fabricated from non-precious metals.

The addition to teeth of prosthetic structures, such as for example, an arrangement of at least two crowns secured together, are well known in the art. However, these crowns are wholly fabricated from metals capable of being soldered, in most cases precious metals, where the crown are investment molded. At the present time, the cost of precious metals has risen sharply, being at least five times or more the price of a few years ago. Accordingly, the cost of the precious metal has greatly increased the cost of the crowns fabricated therefrom.

Several attempts have been made to solve this cost problem, however these attempts usually create additional problems. Attempts have been made to fabricate the crowns from non-precious metals, but it has been found that these crowns cannot be soldered together, so that alternate methods must be used to secure the nonprecious metal crowns together. Such methods as using locking pins, interlocking keys, bridge members and screw threaded means have been employed, but these are not easily handled by the dentist and usually result in an increased cost in the manufacture thereof and the labor involved.

SUMMARY OF THE INVENTION

This invention relates to soldering tabs for investment molded crowns fabricated from non-precious metals and disposed on at least two adjacent teeth, each of the tabs being fabricated from metal means capable of being soldered, the metal means being a precious metal, each tab including securing means for anchoring the respective tab in a non-solderable metal of which the crowns are fabricated, at least one of the tabs being disposed in each crown at an outer wall of the crown facing another of the tabs disposed in an adjacent crown at a proximal outer wall of the adjacent crown to permit the facing tabs to be soldered together to fix the adjacent crowns relative to each other. The securing means includes tapering walls defining a wedge-shaped portion. Each of the tabs is provided with threaded opening means extending through front and rear walls of each tab for receiving a threaded member to position the tab during investment molding of the crowns and for receiving solder when the facing tabs are secured together.

Accordingly, an object of the present invention is to provide soldering tabs for investment molded crowns fabricated from non-precious metals which overcomes the disadvantages of the prior art.

Another object of the present invention is to provide soldering tabs as mentioned above which are fabricated from metal capable of being soldered, preferably from a precious metal.

A further object of this invention is to provide soldering tabs as mentioned above which include securing means for anchoring the respective tabs in the non-solderable metal of the crowns, where these securing means are preferably provided by tapering walls defining a wedge-shaped portion.

A still further object of the present invention is to provide soldering tabs as mentioned above which are provided with threaded opening means extending through each tab for receiving a threaded member to position the tab during investment molding of the crowns and for receiving solder when the facing tabs are secured together.

An added object of this invention is to provide soldering tabs as mentioned above that are simple, inexpensive and can easily be manufactured, and which provide the desired securement between adjacent crowns.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DESCRIPTION OF THE PREFERRED EMBODIMENT

Figure 1:
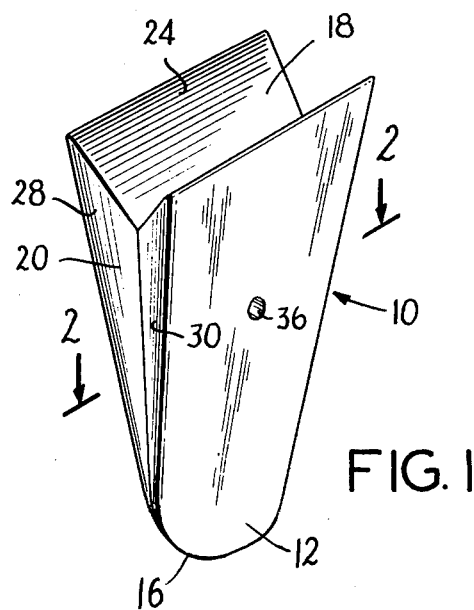
FIG. 1 represents a perspective view of a soldering tab pursuant to the present invention.
Figure 2:
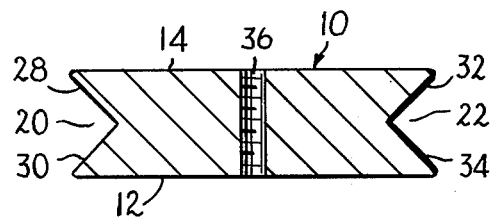
FIG. 2 represents a sectional view, taken on the line 2—2 of FIG. 1.

Referring to the drawings, FIGS. 1 and 2 illustrate a soldering tab 10 of the present invention. The tab 10 includes a front wall 12 and a rear wall 14 which converge or taper towards each other to form a rounded or curved bottom edge 16, the front and rear walls being furthest apart at the wider top portion of the tab. Preferably, the front and rear walls 12, 14 are flat to define planar surfaces.

The tab 10 is fabricated from a metal or alloy capable of being soldered. Preferably, the metal is a precious metal or alloy, such as gold, silver or platinum, or alloys including same, which are traditionally used in the dental art.

Each of the top wall 18 and side walls 20, 22 include a pair of wedge-shaped surfaces which taper or converge towards each other into the body of the tab 10. The surfaces 24 and 26 define the top wall 18, the surfaces 28 and 30 define the side wall 20, and the surfaces 32 and 34 define the other side wall 22. As best shown in FIG. 2, a threaded opening or hole 36 extends through the tab 10 from the front wall 12 to the rear wall 14, the function of which will be set forth hereinafter below in more detail.

As generally understood, dental crowns are molded to their desired shape for positioning or attachment to previous prepared teeth by an investment molding process, which is well known in the art so that only a brief discussion of such molding steps and details is required herein. A crown form 38 fabricated from wax is prepared in the usual manner, well known in the art. The tab 10 is pressed against the soft wax of the crown form 38 until the front face 12 of the tab 10 has been brought into its desired outer position and the surplus wax is trimmed away. The desired position of the tab 10 is defined by an outer location on the crown form 38 which is to be proximal to an adjacent portion of a crown for the next succeeding tooth, in such a manner that these outer surfaces will be in abutting relationship.

Figure 3:
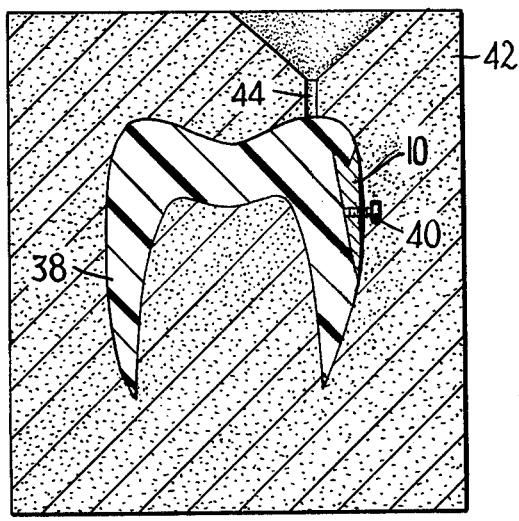
FIG. 3 represents a sectional view of an investment mold filled with a wax crown having a soldering tab of the present invention thereon.
Figure 5:
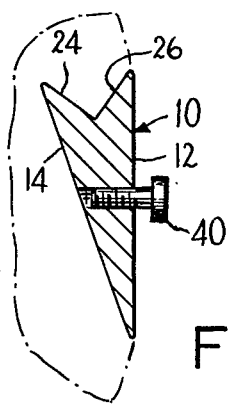
FIG. 5 represents an enlarged sectional view of the soldering tab shown in FIGS. 3 and 4.

A positioning pin 40, having an enlarged head and a threaded end portion, is threaded into the tab opening 36, as best shown in FIG. 5. Preferably, the pin 40 does not extend entirely through the tab 10, being slightly spaced from the rear wall 14. Investment material 42 is applied to the assembled crown form 38 and tab 10 to completely surround the assembled unit, except for the crucible and sprue channel 44 which are formed in the usual manner, to provide the investment mold as shown in FIG. 3. The crucible former and the sprue are removed after the investment material 42 has set, leaving the sprue channel 44, such procedure being well known in the art.

Figure 4:
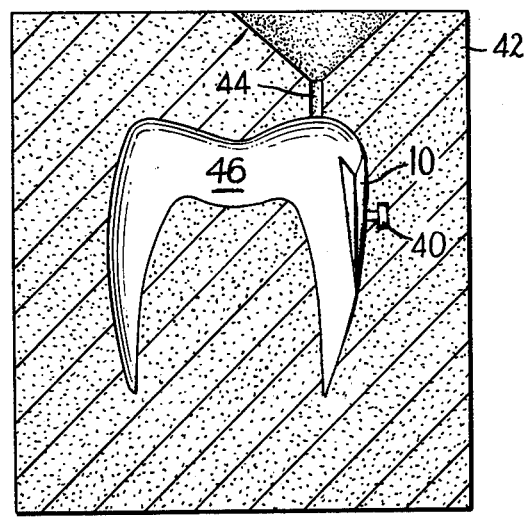
FIG. 4 represents a sectional view of the investment mold of FIG. 3 with the wax burned out.

The investment mold and its contents are heated, and the wax crown form 38 is melted and driven off, leaving the void 46, as shown in FIG. 4, which is to be filled with the moltent metal. However, the tab 10, secured to the investment material by the positioning pin 40, remains in the investment mold. The enlarged head of the pin 40 provides the desired securement of the tab 10 in the investment material 42, so that the tab 10 cannot be separated or dislodged from its position within the investment mold.

Figure 6:
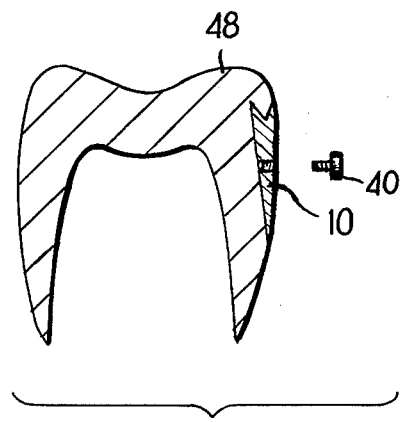
FIG. 6 represents a sectional view of a crown having a soldering tab anchored therein.
Figure 7:
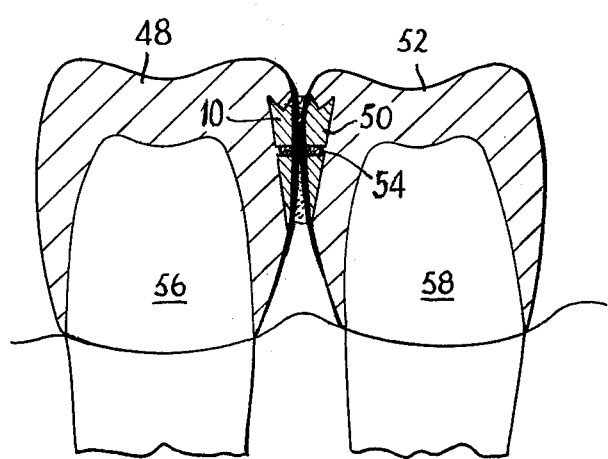
FIG. 7 represents a sectional view of a dental prosthetic structure having two crowns secured together by the soldering tabs of the present invention.

The moltent metal of a non-precious material is poured through the sprue canal 44 into the void 46, where the exhausting air passes through the pores of the investment material 42 and causes the moltent metal, as it is poured, to enter all portions of the void 46. When the metal is poured in this way, it fills each of the wedge-shaped areas of the tab 10, in addition to filling that portion of the threaded opening 36 which is not occupied by the pin 40, to provide a solid connection or anchor between the formed non-precious metal crown 48 and the tab 10, as shown in FIG. 6. Consequently, the crown 48 closely and accurately assumes the same shape as the wax crown form 38.

The non-precious metal is preferably fabricated from a stainless steel alloy, chromium-nickel alloy, or cobalt-chromium alloy or like materials which are considerably less expensive than the gold and platinum alloys which have traditionally been used in the dental art. Hence, the present invention is of considerable economic importance.

When the metal forming the crown 48 has cooled, the crown 48 with the tab 10 secured therein is removed from the investment mold in a conventional manner. Once removed from the mold, the pin 40 is removed from the tab 10 as the function thereof has already been performed.

Figure 8:
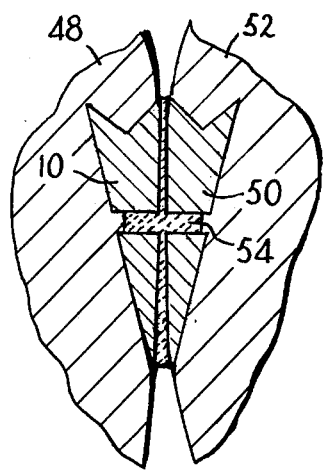
FIG. 8 represents an enlarged sectional view of the soldering tabs shown in FIG. 7.

In a similar manner as mentioned above, a tab 50 is secured or anchored in a crown 52, the crown 52 having been prepared for an adjacent tooth. The tab 10, disposed at the outer wall of the crown 48, is positioned facing the tab 50, disposed in the outer wall of the crown 52, in a proximal relationship thereto to permit the facing tabs to be soldered together to fix the adjacent crowns 48, 52 relative to each other. A soldering material 54, or any other similar suitable material known in the art, is disposed between the facing tabs 10, 50 and heated in a conventional manner to fuse the tabs 10, 50 together as best shown in FIG. 8. As illustrated, the soldering material 54 in addition to being disposed between the planar outer surfaces of the tabs 10, 50, also fills the major remaining unfilled tab opening 36, to provide additional securement between the tabs.

It is a simple matter to affix the secured together crowns 48, 52 to the prepared teeth 56, 58 respectively, by cement or other material well known in the art. It is understood, that the same above mentioned process would be followed if three or additional crowns are required to be secured together, where the intermediate crown or crowns would be provided with two soldering tabs on opposite sides thereof for securement to the tabs of the adjacent crowns on each side thereof.

Thus, from the foregoing, it should be readily appreciated that there has been described not only a noteworthy dental prosthetic structure consisting of at least two crowns 48, 52 secured together by the soldering tabs 10, 50, but also a noteworthy article of manufacture consisting of the soldering tab and a removable pin connected thereto which during the investment molding thereof positions and secures the tab in the investment material.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. Soldering tabs for investment molded crowns fabricated from non-precious metals and disposed on at least two adjacent teeth, comprising each of said tabs being fabricated from metal means capable of being soldered, said metal means comprising a precious metal, each tab including securing means for anchoring the respective tab in a non-solderable metal of which the crowns are fabricated, at least one of said tabs being disposable in each crown at an outer wall of the crown facing another of said tabs disposed in an adjacent crown at a proximal outer wall of the adjacent crown to permit the facing tabs to be soldered together to fix the adjacent crowns relative to each other.

2. Soldering tabs as claimed in claim 1, wherein each of said tabs includes a front wall and a rear wall, said front wall being provided with a planar surface, said planar surface of said one tab facing said planar surface of said another tab.

3. Soldering tabs as claimed in claim 2, wherein said front wall and said rear wall converge towards each other to provide a wide portion at one end and a narrower portion at an opposite end of each tab.

4. Soldering tabs as claimed in claim 3, wherein said wide portion include tapering walls to define a wedge-shaped end portion, said securing means including said wedge-shaped end portion whereby said tapering walls are anchored in the crowns.

5. Soldering tabs as claimed in claim 4, wherein each of said tabs includes side walls disposed between said front and rear walls, each of said side walls including tapering surfaces to define wedge-shaped side portions, said securing means further including said wedge-shaped side portions for anchoring said tabs in respective crowns.

6. Soldering tabs as claimed in claim 5, wherein each of said tabs is provided with threaded opening means extending through said front and rear walls of each tab for receiving a threaded member to position said tab during investment molding of the crowns and for receiving solder when said facing tabs are secured together.

7. Soldering tabs as claimed in claim 1, wherein each of said tabs is provided with threaded opening means extending through each tab for receiving a threaded member to position said tab during investment molding of the crowns and for receiving solder when said facing tabs are secured together.

8. Soldering tabs as claimed in claim 1, wherein said securing means includes wedge-shaped portions provided in side walls of each of said tabs.

9. Soldering tabs as claimed in claim 8, wherein said securing means further includes wedge-shaped portions provided in a wide end of said of said tabs.

* * * * *